United States Patent [19]

Baron

[11] Patent Number: 4,461,294

[45] Date of Patent: Jul. 24, 1984

[54] APPARATUS AND PROCESS FOR RECURVING THE CORNEA OF AN EYE

[76] Inventor: Neville A. Baron, Medical Plaza - #66 Rte. 46, Dover, N.J. 07801

[21] Appl. No.: 340,978

[22] Filed: Jan. 20, 1982

[51] Int. Cl.³ .............................................. A61B 17/36
[52] U.S. Cl. .................................. 128/303.1; 128/395
[58] Field of Search ...................... 128/303.1, 395–398

[56] References Cited

U.S. PATENT DOCUMENTS 3,703,176 11/1972 Vassiliadis et al. ................. 128/395
3,783,874 1/1974 Koester et al. ..................... 128/395
3,900,034 8/1975 Katz et al. .......................... 128/395

FOREIGN PATENT DOCUMENTS 563751 12/1977 U.S.S.R. ........................... 128/303.1

Primary Examiner—Lee S. Cohen

[57] ABSTRACT

The cornea of an eye is recurved by disposing therein light-absorbing color bodies and thereafter vaporizing such color bodies according to a pre-selected design to form corneal-recurving scars.

6 Claims, 1 Drawing Figure

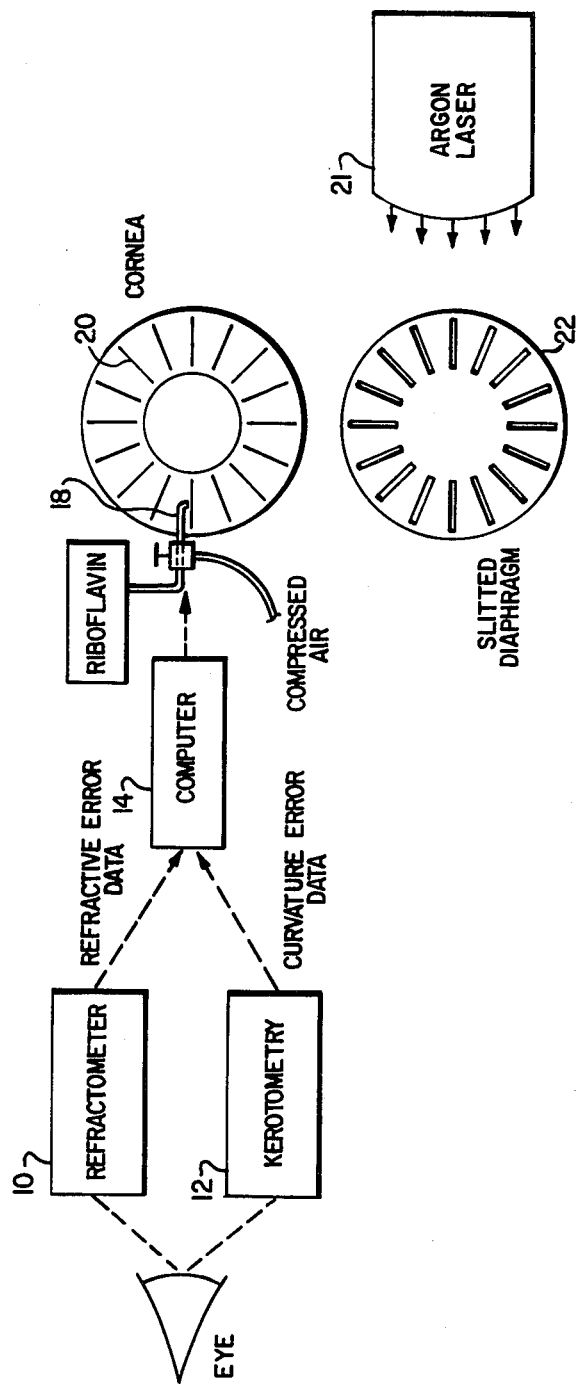

APPARATUS AND PROCESS FOR RECURVING THE CORNEA OF AN EYE

BACKGROUND OF THE INVENTION

This invention relates to an apparatus and process for recurving the cornea of an eye.

It has previously been proposed to recurve the cornea of an eye by a surgical procedure (radial keratotomy) in which spoke-like incisions are made in the cornea using microsurgery techniques. However, this procedure is difficult to control precisely.

It has also previously been proposed to utilize light energy (transmitted through the iris in some instances) to effect photocoagulation in the treatment of surface, skin, and conjunctival lesions, anterior chamber and iris lesions, and retinochoroidal diseases, as well as retinal tears. In this regard it has been reported that problems encountered with inadvertent overheating of the anterior segment secondary to photocoagulation include serofibrinous iritis, posterior and anterior synechias, corneal endothelial edema, swelling of the corneal stroma, epithelial corneal edema, secondary glaucoma, iris atrophy, corneal dystrophy, and progressive cataract. It has also been stated that sufficient absorption of light energy by the iris may lead to iris atrophy, irregularity of the pupil, and other symptons, that excessive photocoagulation may cause tissue shrinkage leading to traction or displacement of tissues, and that "Without direct treatment to the cornea, corneal leukomas, which are usually transient, and corneal neovascularization rarely have been reported with an inadequately dilated pupil." (See "Clinical Ophthalmology," Vol. 5, Chap. 9, pp. 8 and 9, published 1976 by Harper & Row, Publishers, Inc., Hagerstown Md.)

SUMMARY OF THE INVENTION

In accordance with the present invention, apparatus for recurving the cornea of an eye comprises means for disposing light-absorbing color bodies in a cornea, and a laser adapted to vaporize said color bodies from said cornea according to a predetermined design, whereby recurving scars are generated in said cornea in accordance with said predetermined design.

Also in accordance with the present invention is a process for recurving the cornea of an eye which comprises disposing light-absorbing color bodies in a cornea according to a preselected design and thereafter vaporizing at least a portion of said design by applying energy thereto sufficient to effect vaporization thereof and generate thereby formation of scar tissue to form corneal-recurving scars in said cornea according to said preselected design.

BRIEF DESCRIPTION OF THE DRAWING

The sole FIGURE shows the basic apparatus for carrying out the method of the invention.

DETAILED DESCRIPTION OF THE INVENTION

In carrying out the present invention according to a preferred embodiment thereof, the refractive error of the eye to be corrected is determined using a refractometer 10 in the usual manner. The existing curvature of the cornea is ascertained as customary by the use of kerotometry 12. The refractive error and curvature data are entered into a preprogrammed computer 14 which calculates and presents an output representing the requisite number, lengths, depths and relative positions of laser-generated incisions required to correct the corneal curvature. Typically, this pattern will comprise sixteen radial spokes, and will have an outside diameter of about 12 mm. and be toroidal with an inner diameter of about 5 mm., centered on the cornea.

The epithelium layer of the cornea is then debrided (leaving Bowmans membrane intact) using 20% cocaine in saline solution applied manually on a cotton-tipped stick applicator.

Riboflavin dye is then applied to the cornea in bands or spokes according to the previously calculated pattern using an air jet hypodermic injection nozzle 18. The dye penetrates through Bowmans layer and into the stroma to form therein a pigmented centerless starburst of colored bands or spokes 20 according to the pattern precalculated by the computer 14.

The colored bands or spokes embedded in the cornea are thereupon vaporized by exposure to light from an Argon laser 21 adjusted to deliver monochromatic light at a frequency maximally absorbed by the riboflavin, with essentially no injury to other tissues of the eye outside of the cornea.

The laser light is applied through a slitted diaphragm 22 having a pattern of slits corresponding to and aligned with the pattern calculated by the computer and used previously in the application of the riboflavin dye. Thus, the dye and the dye-vaporizing light energy are applied to the cornea according to a single, previously calculated pattern, to generate in the cornea sixteen radially disposed scars corresponding to that pattern.

Alternatively to the use of a slitted diaphragm, fiber optics may be used to deliver laser light to a housing in the shape of a contact lens having a patterned screen in direct contact with the cornea.

Following generation of the desired scar pattern in the cornea as described, antibiotic ointment is applied thereto and the eye is patched until the epithelium regenerates, typically a period of 48–72 hours, thereby establishing a healthy cornea correctively recurved to reduce both myopia and astigmatism.

In an alternate procedure, riboflavin dye is applied as a toroidal design covering the entire cornea with the exception of a 4 mm. diameter central opening centered on the pupil, and laser energy is applied thereto according to the aforesaid calculated design to generate the appropriate scar tissue. Unvaporized riboflavin fades and disperses over the normal course within a period of a few days.

Although riboflavins are the preferred color bodies for use in carrying out the present invention, other color bodies, preferably of a transient nature when applied to the cornea, may also be employed, e.g., red corpuscles recovered from the blood of the person undergoing corneal recurvature.

Similarly, although laser energy is preferred for use as an energy source in that a wavelength may be selected which is maximally absorbed by the color body applied to the cornea, other monochromatic, filtered, or broad spectrum sources (such as an electric arc) may likewise be employed for the purpose.

What is claimed is:

1. A process for recurving the cornea of an eye which comprises disposing light-absorbing color bodies in the cornea and thereafter vaporizing at least a portion of said color bodies by applying energy thereof sufficient to effect vaporization thereof, said vaporization being carried out according to a predetermined pattern and generating thereby corneal-recurving scar tissue in said cornea according to said predetermined pattern.

2. A process for recurving the cornea of an eye which comprises disposing light-absorbing color bodies in the cornea according to a preselected design and thereafter vaporizing at least a portion of said design by applying energy thereto sufficient to effect vaporization thereof, and generating thereby formation of scar tissue to form corneal-recurving scars in said cornea according to said preselected design.

3. A process for predictably recurving the cornea of an eye which comprises embedding light-absorbing color bodies in the light-transparent stroma layer of a cornea according to a preselected patterned design and thereafter vaporizing said color bodies by applying laser-generated light energy thereto, thereby generating corneal-recurving scars in said cornea according to said preselected patterned design.

4. A process as set forth in claim 3 in which said laser-generated light is applied to said cornea according to a pattern identical to said preselected patterned design.

5. A process as set forth in claim 3 in which said color bodies are riboflavin and said laser-generated light is generated at a frequency maximally absorbed by said riboflavin.

6. An apparatus for recurving the cornea of an eye comprising a first monochromatic light-emitting laser means, said monochromatic light being adapted to vaporize color bodies from a cornea containing said color bodies and thereby effect scar formation in said cornea, and second means associated with said first laser means to deliver said monochromatic light to said color body-containing cornea in a selected pre-calculated toroidal pattern having an outside diameter of about 12 mm. and an inner diameter of about 5 mm., whereby said scar formation corresponds to said selected pattern.

* * * * *